United States Patent [19]

Joukou et al.

[11] Patent Number: 4,880,774

[45] Date of Patent: Nov. 14, 1989

[54] SUSTAINED RELEASE AROMATIC

[75] Inventors: Isao Joukou; Ayako Sekikawa; Hideo Sugi; Kenji Tahara, all of Kanagawa, Japan

[73] Assignee: Kurita Water Industries, Ltd., Tokyo, Japan

[21] Appl. No.: 179,085

[22] Filed: Apr. 8, 1988

[30] Foreign Application Priority Data

Apr. 14, 1987 [JP] Japan .................................. 62-91771
Feb. 24, 1988 [JP] Japan .................................. 63-41289

[51] Int. Cl.[4] .................................................. A61K 7/46

[52] U.S. Cl. ........................................... 512/2; 512/3; 512/4

[58] Field of Search .................................... 512/2, 3, 4

[56] References Cited

U.S. PATENT DOCUMENTS

| | | | |
|---|---|---|---|
| 3,994,439 | 11/9176 | Van Breen et al. | 512/4 |
| 4,199,481 | 4/1980 | Hall et al. | 512/3 |
| 4,356,115 | 10/1982 | Shibanai et al. | 512/4 |

FOREIGN PATENT DOCUMENTS

| | | | |
|---|---|---|---|
| 1124180 | 5/1981 | Canada | 512/4 |
| 0013688 | 8/1980 | European Pat. Off. | 512/4 |
| 58-141152 | 8/1984 | Japan | 512/4 |
| 61-37721 | 2/1986 | Japan | 512/4 |
| 61-152765 | 7/1986 | Japan | 512/4 |

*Primary Examiner*—James H. Reamer
*Attorney, Agent, or Firm*—Kanesaka and Takeuchi

[57] ABSTRACT

A sustained release aromatic comprises a clathrate compound composed of a perfume and a polyphenyl compound and gives out fragrance slowly but steadily over a long period of time. It is produced by a process comprising melting under heat a perfume which is a solid at an ordinary room temperature, and adding a polyphenyl compound to the molten perfume. Alternatively, a perfume which is a liquid at an ordinary room temperature is mixed with a polyphenyl compound so that they may react with each other, and a solid reaction product is separated from their mixture.

2 Claims, 7 Drawing Sheets

VARIATION RATE IN THE WEIGHT (%)
100
80
60
40
20
0
0
10
20
30
40
TIME (DAY)

● : EXAMPLE 4
□ : EXAMPLE 5
■ : EXAMPLE 6
○ : EXAMPLE 7
TIME (hr)
VARIATION RATE IN THE WEIGHT (%)
0
50
100
150
200
0
20
40
60
80
100

(%)
100
90
80
70
60
50
40
30
20
10
0
4000 3800 3600 3400 3200 3000 2800 2400 2000 1800 1600 1400 1200 1000 800 600 400 (cm⁻¹)

SUSTAINED RELEASE AROMATIC

BACKGROUND OF THE INVENTION

1. Field of the Invention

This invention relates to a novel sustained release aromatic, which can stably give out fragrance continuously for a certain length of time, and a process for manufacturing thereof.

2. Description of the Prior Art

Three types of aromatics are available for use in a living room in a residence, a hotel room or lobby, an automobile, a washroom, etc. They are a solid aromatic, a liquid aromatic and an aromatic in aerosol form.

A typical solid aromatic is a plasticized product formed from a mixture of a perfume, a plasticizer, a stabilizer and a porous powder. It is often used not only for giving out fragrance, but also as one of the articles for decorating the interior of a room.

A container for holding a liquid aromatic has a top opening provided with a piece of felt, filter paper, or other material for drawing up the aromatic and causing it to volatilize at a contolled rate to give out fragrance.

An aromatic in aerosol form is sprayed to give out a certain kind of fragrance instantly and effectively. It is classified into two types depending on the base which it contains. One of them contains chlorofluorocarbon and alcohol as the base, and the other LPG and water (with a surface active agent).

All of these aromatics, however, have their own drawbacks. The solid aromatic hardly permits the use of any perfume having a low boiling point, since its manufacture employs heat. The liquid aromatic is split if its container is turned over. The aromatic in aerosol form permits the use of only limited kinds of perfumes. It is necessary to avoid the use therefor of any perfume of the type which may undergo a chemical change or corode a can containing the aromatic, since it is likely to result in an undesirable change of fragrance or the clogging of a valve which is due to the loss of emulsion stability.

There is also known a sustained release solid aromatic formed from a synthetic resin containing a clathrate compound obtained by the inclusion of a perfume in cyclodextrin, and sugar-alcohol, as disclosed in Japanese Laid-Open Patent Specification No. 142765/1986.

SUMMARY OF THE INVENTION

Under these circumstances, it is an object of this invention to provide an improved sustained release aromatic which can overcome all of the drawbacks of the prior art as hereinabove pointed out.

This object is attained by an aromatic which contains a clathrate compound composed of a perfume and a polyphenyl compound. The aromatic of this invention is particularly characterized by the improved life and stability of the perfume which it contains.

It is another object of this invention to provide a process which is beneficial for the industrial production of an improved sustained release aromatic.

This object is attained by a process which comprises melting under heat a perfume which is a solid at an ordinary room temperature, and adding a polyphenyl compound to the molten perfume.

It is also possible to produce an improved sustained release aromatic by mixing a perfume which is a liquid at an ordinary room temperature, and a polyphenyl compound, and separating a solid product from their mixture.

DETAILED DESCRIPTION OF THE INVENTION

Figure 1:
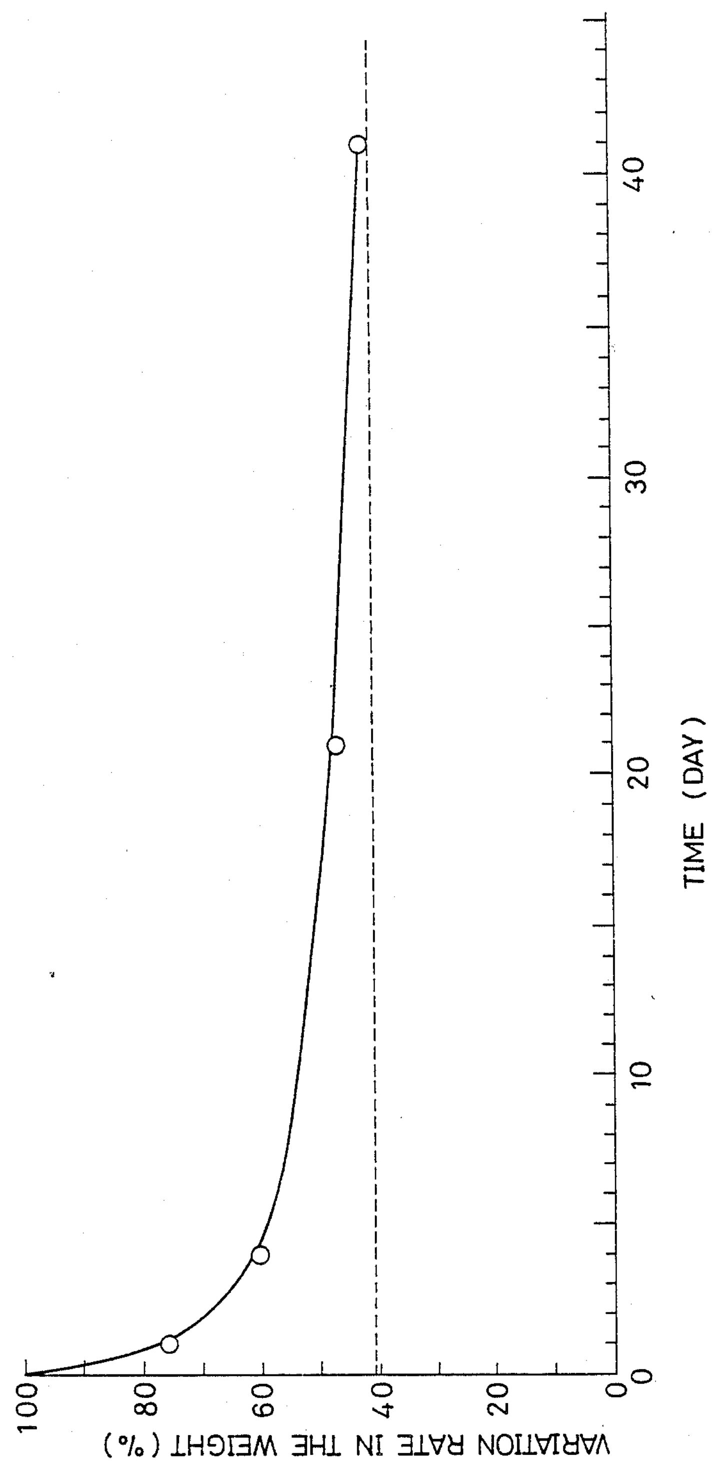
FIG. 1 is a graph showing the results of the measurements which will hereinafter be described in EXAMPLE 1.

The aromatic of this invention contains a clathrate compound which is formed by the inclusion of the guest molecules of a perfume in the host molecules of a polyphenyl compound.

The perfume may be made of any kind if it is fragrant. It may, for example, be a liquid perfume such as cineole (1,8-cineole), hinokiol consisting mainly of hinokitiol, essence of a fragrant olive, jasmin, lemon essence, essence of cinnamon leaves, quassia oil, methanol, rose, rosemary, palmarosa oil, lavender oil, spearmint oil, mentha arbensis, l-α-terpineol, l-menthone, citronellal, d-pulegone, linalool oxide, Ceylon cinnamon, peppermint oil and l-carvone. A terpene perfume, such as menthol or l-α-terpineol, can be used in its solid form, too. It is also possible to use a mixture of two or more kinds of perfumes, if required.

The polyphenyl compound is selected from a wide range of carbocyclic compounds having two or more benzene nuclei. They include not only a compound having a plurality of phenyl or phenylene groups, or other aromatic groups having a valence of three or more, but also condensed polycyclic compounds such as naphthalene compounds.

Specific examples of the polyphenyl compounds include the following:

(I) 1,1,6,6-tetraphenyl-2,4-hexadiyne-1,6-diol (I)

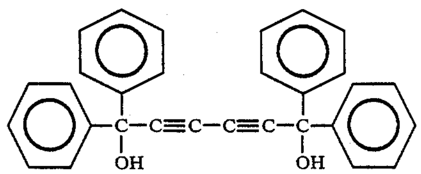

(II) 1,1-di(2,4-dimethylphenyl)-2-propyne-1-ol

-continued

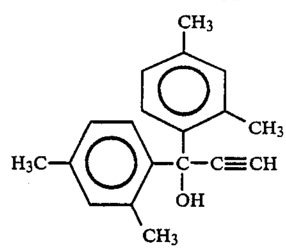

(II)

(III) 1,1-bis(4-hydroxyphenyl)-cyclohexane

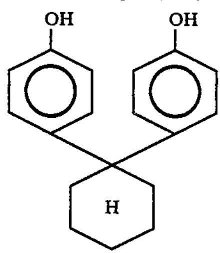

(III)

(IV) N,N,N',N'—tetra(cyclohexyl)-(1,1'-biphenyl)-2,2'-dicarboxyamide

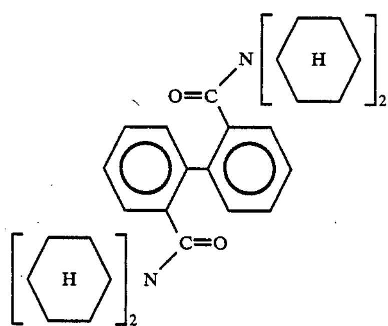

(IV)

(V) Bis(4-hydroxyphenyl)sulfone

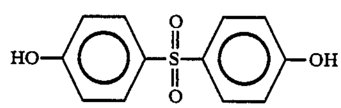

(V)

(VI) 4,4'-butylidenebis(6-tert-butyl-3-methylphenol)

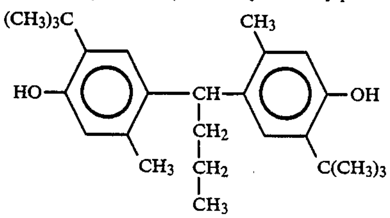

(VI)

(VII) 2,2'-methylenebis(6-tert-butyl-4-methylphenol)

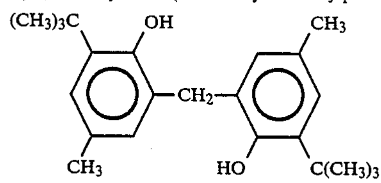

(VII)

(VIII) 4,4'-thiobis(6-tert-butyl-3-methylphenol)

-continued

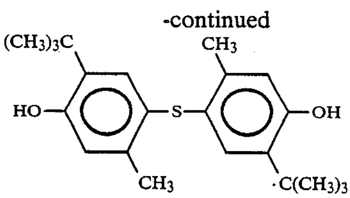

(VIII)

(IX) 1,1,4,4-tetraphenyl-2-butyne-1,4-diol

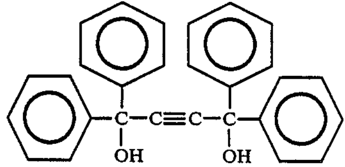

(IX)

(X) 1,1'-bi-2-naphthol

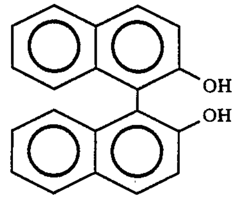

(X)

(XI) 1,1,6,6-tetra(2,4-dimethylphenyl)-2,4-hexadiyne-1,6-diol

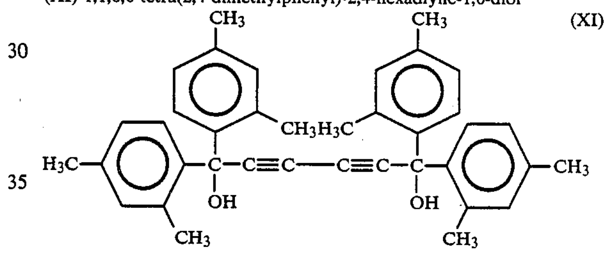

(XI)

(XII) 9,10-di(4-methylphenyl)-9,10-dihydroanthracene-9,10-diol

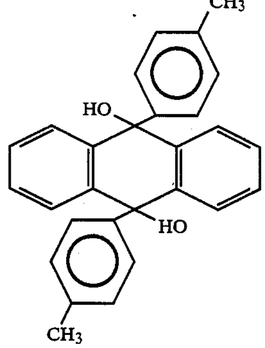

(XII)

(XIII) 1,1,2,2-tetraphenylethane-1,2-diol

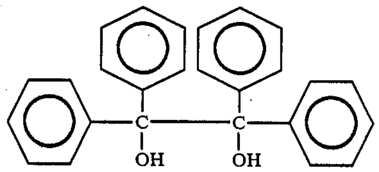

(XIII)

A clathrate compound can be prepared easily by a process which comprises melting a perfume under heat if it is a solid at an ordinary room temperature, and adding a polyphenyl compound to the molten perfume. The perfume is heated to a temperature which is higher than its melting point. For example, hinokitiol has a melting point of 51° C. to 52° C. and is, therefore, heated to a temperature of, say, 55° C. to 60° C. over a water bath. If l-α-terpineol is used, it is heated to a temperature of 45° C. to 65° C. over a water bath, as it has a melting point of 38° C. to 40° C.

Then, the powder of a polyphenyl compound is added directly into the molten perfume and they are mixed under stirring. They are reacted with each other at a temperature which is not lower than the temperature at which the perfume can remain in its molten state, and not higher than 100° C. Their reaction is continued for a period of, say, 1 to 60 minutes. A period of about five minutes is usually sufficient. When the product of the reaction has been solidified, it is cooled to an ordinary room temperature, so that the reaction may be terminated. The infrared spectrum of the product makes it possible to ascertain that it is a clathrate compound.

If a liquid perfume is used, a polyphenyl compound having an appropriate molar ratio to the perfume is brought into direct contact therewith. A clathrate compound is precipitated if the polyphenyl compound is admixed with the perfume. The precipitate can be separated from the liquid easily by a customary method. The reaction between the perfume and the polyphenyl compound is continued for a period of, say, 1 to 120 minutes at a temperature of 0° to 50° C. The infrared spectrum of the solid product can be used to ascertain that it is a clathrate compound.

The process of this invention as hereinabove described does not require any organic or other solvent for dissolving the polyphenyl compound. Therefore, it can overcome any problem that might result from the use of any such solvent.

The perfume does not always need to be a purified product not containing impurities, but may contain some impurities. The reaction between the perfume and the polyphenyl compound according to this invention is so selective that even if the perfume may contain impurities, only the desired component of the perfume is included in the polyphenyl compound to form the aromatic of this invention.

The aromatic of this invention can be produced by other processes, too. A solid perfume is brought into contact with a solution prepared by dissolving a polyphenyl compound in a solvent such as methanol, ethanol, n-propanol, acetone, benzene, chloroform, ethyl acetate or other ester, or dipropyl ether or other ether, so that the perfume may react with the polyphenyl compound. Then, the solvent is removed from the solution by evaporation, or the solution is left at a standstill, whereby a clathrate compound is precipitated. The precipitated compound is separated from the solution by filtration in a customary way to yield a constantly fragrant aromatic.

Alternatively a solid perfume is dissolved in any of the solvents which have hereinabove been listed as being used for dissolving a polyphenyl compound, and a polyphenyl compound is added to the solution of the perfume.

The aromatic of this invention can be produced not only by the liquid to liquid reaction or the solid to liquid reaction, but also by the solid to solid reaction which involves a solid perfume and a solid polyphenyl compound.

The aromatic of this invention may contain a clathrate compound which is composed of a perfume and a polyphenyl compound, or may contain two or more clathrate compounds each containing a perfume or a polyphenyl compound. The aromatic of this invention is usually a solid in powder form and is easy to mold into a particular shape. It is easily possible to change the size of the area in which the aromatic contacts the air, and thereby the degree to which it gradually gives out fragrance, if the particle size of the powder, the shape of the molded product, etc. are appropriately altered.

The aromatic of this invention can be used in a variety of ways as will hereunder be stated by way of example:

(1) The powder is placed in a container having an opening or openings;

(2) The powder is molded into an appropriate shape;

(3) A mixture of the aromatic with a paint, or other resin is coated on an appropriate material; or (4) The aromatic is caused by an appropriate method to the surface of an appropriate object.

The sustained release aromatic of this invention is a solid, since the perfume forms a clathrate compound with the polyphenyl compound. Therefore, it has no possibility of being split when its container has been turned over, and is easy to handle.

As the perfume is imprisoned in the clathrate compound, its aroma is diffused so slowly that the aromatic of this invention is effective for constant use over a long period of time. If the particle size of the powdery clathrate compound is appropriately changed, it is possible to vary the surface area of its particles which is exposed to the air, and thereby the rate at which the aroma is diffused. The aroma has a lower rate of diffusion if the compound has a larger particle size. The powdery compound can be molded into a wide variety of shapes and is, therefore, useful for a wide variety of applications including the fabrication or preparation of the following:

(1) Fragrant articles for decorating the interior of a room or automobile;

(2) Fragrant building material or flooring;

(3) Fragrant furniture;

(4) Fragrant bedding;

(5) Toiletry (cosmetics, materials used in a bathroom, soap, toothpaste, etc.);

(6) Fragrant toys;

(7) Fragrant outfittings (8) Fragrant accessories;

(9) Fragrant stationery and office supplies; and

(10) Fragrant articles for sanitary use.

After the perfume has finished giving out all of its aroma, the host compound can be reused for preparing a fresh aromatic if it is brought into contact with a fresh perfume.

The aromatic of this invention has a number of advantages including the following:

(1) It can maintain its fragrance for a long period of time, as the perfume is diffused into the air only slowly;

(2) As it is a solid, it is easy to handle and mold into a desired shape; and (3) The rate at which the aroma is diffused can be controlled easily if, for example, the particle size of the clathrate compound is appropriately varied.

The process of this invention does not essentially require the use of any solvent for producing the improved aromatic of this invention. Therefore, it facilitates the production of the aromatic at a low cost with a high degree of selectivity and a high yield, for the following reasons:

(1) There is no necessity for selecting a solvent;

(2) The costs of materials and production can be reduced accordingly;

(3) The conditions under which the aromatic is produced are easy to establish;

(4) The reaction process can be simplified, as it does not essentially require any step of separating a solid from a liquid; and (5) People engaged in the production of the aromatic and their working environment can be protected from any contamination by an organic solvent.

The invention will now be described more specifically with reference to a wide variety of examples thereof. It is, however, to be understood that the following examples are not intended for limiting the scope of this invention:

EXAMPLE 1

5 gram of 1,1-bis(4-hydroxyphenyl)-cyclohexane were placed in a 30 ml Erlenmeyer flask and 9.6 ml of 1,8-cineole ($C_{10}H_{18}O$; a colorless liquid having a molecular weight of 154 and a special smell similar to that of camphor) were added into the flask at a temperature of 25° C. The amount of the guest compound was three times as large by molar ratio as that of the host compound. The reaction system which had thereby been established was composed of a suspension containing the host and guest compounds. The reaction proceeded as the suspension was stirred for several minutes, and after several more minutes, it solidified instantaneously. The solifidified product was crushed into fine particles. The particles were placed in a Buchner funnel, washed with 5 ml of benzene, and subjected to filtration under suction by an aspirator for about an hour. The solid which had been obtained by the filtration had a smell peculiar to cineole and similar to that of camphor. The examination of the solid through an electron microscope revealed that it was a crystalline substance. The NMR analysis of the solid indicated that it contained 1,1-bis(4-hydroxyphenyl)-cyclohexane and cineole in a molar ratio of about 1 to 2.5 (or 40.9% and 59.1%, respectively, by weight).

A sample was prepared by crushing the solid into fine particles having a diameter not exceeding about 1 mm. 4 gram of the sample were placed in a laboratory dish (Schale) having a diameter of 80 mm in an environment having an ordinary room temperature and an atmospheric pressure. A variation in the weight of the sample was measured to determine the rate of diffusion of the aroma. The weight $W_1$ of the sample was measured after a certain length of time and compared with its initial weight $W_0$, whereby the value of $$\frac{W_1}{W_0} \times 100\ (\%)$$

was obtained. The higher the rate of diffusion, the greater reduction of weight the sample showed in relation to the length of time which had elapsed.

The results are shown in FIG. 1. As is obvious therefrom, the aromatic continued giving out fragrance for a period of over 40 days.

EXAMPLE 2

The powdery aromatic which had been obtained in EXAMPLE 1 was compared with 1,8-cineole with respect to the rate of diffusion of aroma in an environment having a temperature of 40° C. and a reduced pressure of 50 mm Hg. Only one hour had elapsed before 65% by weight of the 1,8-cineole was diffused. On the other hand, it was only 18% by weight of the cineole in the product of EXAMPLE 1 that had been diffused before an hour elapsed, and as long as eight hours had elapsed before 65% by weight thereof was diffused.

EXAMPLE 3

A solid particulate clathrate compound was prepared by repeating the process of EXAMPLE 1, but employing hinoki oil consisting mainly of hinokitiol and 1,1-bis(4-hydroxyphenyl)-cyclohexane. The perfume and the polyphenyl compound were employed in a ratio by weight of 50:50. The clathrate compound was compared with a sample consisting solely of hinoki oil with respect to the rate of diffusion of the aroma of hinoki at an ordinary room temperature and an atomospheric pressure. For this purpose, each sample was examined for variation in weight. The results are shown in FIG. 2.

Figure 2:
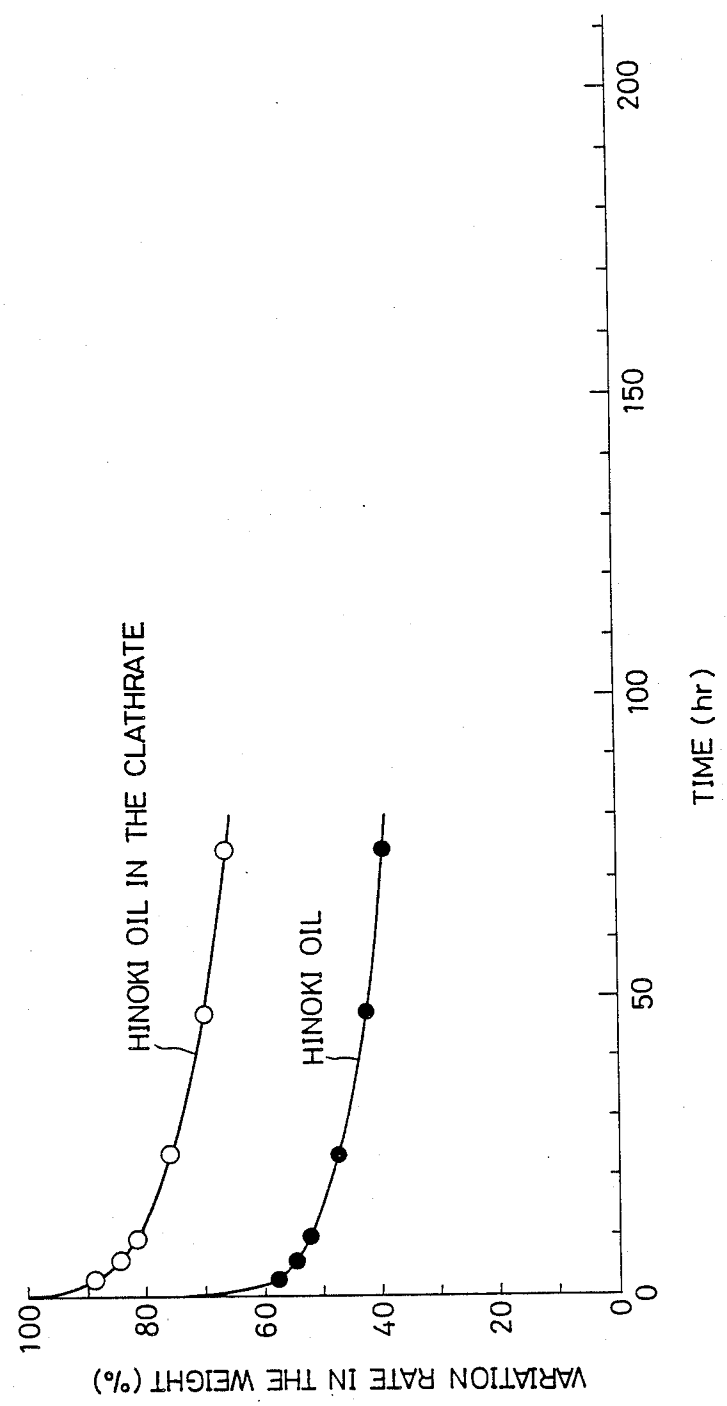
FIG. 2 is a graph showing the results of the measurements which will hereinafter be described in EXAMPLE 3.

As is obvious from FIG. 2, it was when 24 hours elapsed that 52% by weight of the sample consisting solely of hinoki oil had been diffused. On the other hand, it was only 24% by weight of the hinoki oil in the clathrate compound that had been diffused when 24 hours elapsed.

EXAMPLE 4

A 100 ml conical beaker was charged with 15 g of 1,1-bis(4-hydroxyphenyl)-cyclohexane and 10 ml of a liquid perfume having the smell of kinmokusei (fragrant olive) were added into the beaker. The resulting suspension was rapidly stirred with a glass rod at a temperature of 25° C. After several minutes, it solidified. The infrared spectrum of the solidified product indicated that it was a clathrate compound containing 35% by weight of kinmokusei. It had the smell of kinmokusei.

A sample was prepared by crushing the solid product into fine particles having a diameter not exceeding about 1 mm. Four grams of the sample were placed in a laboratory dish having a diameter of 80 mm in an environment having an ordinary room temperature and an atmospheric pressure. A variation in weight of the sample was measured to determine the rate at which the perfume was diffused. The results are shown in FIG. 3.

Figure 3:
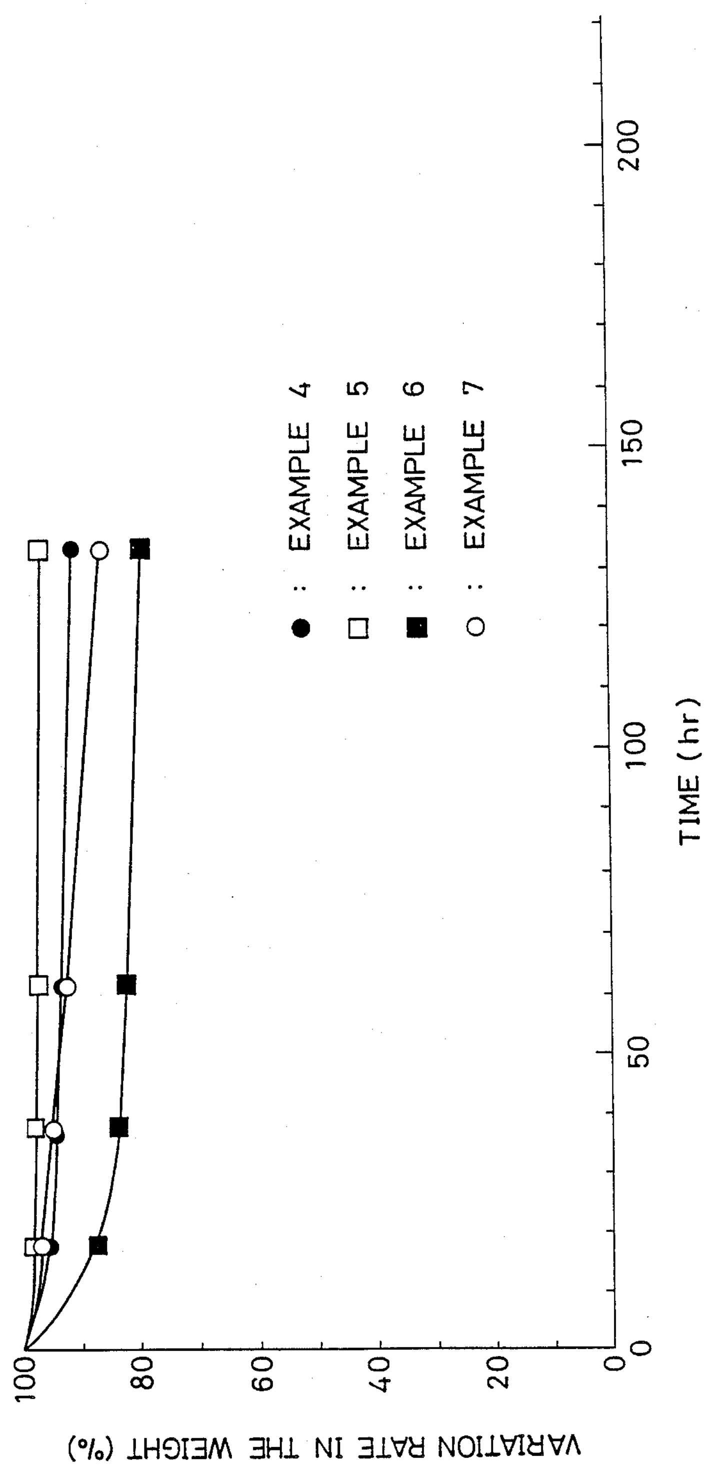
FIG. 3 is a graph showing the results of the measurements which will be described as having been obtained in EXAMPLES 4 to 7.

As is obvious from FIG. 3, the sample has 90.8% of its initial weight when 134 hours elapsed, or reduced only 9.2% of its weight during the 134 hours. This reduction in weight meant a reduction of 26% in weight of the perfume which the sample contained. In other words, it still contained 74% of the initial weight of the perfume.

EXAMPLE 5

A clathrate compound was prepared by repeating the process of EXAMPLE 4, except that a liquid perfume having the smell of jasmin was employed. The infrared spectrum of the solidified product indicated that it was a clathrate compound containing 38% by weight of jasmin. It had the smell of jasmin.

The procedure of EXAMPLE 4 was also repeated for determining the rate of diffusion of the perfume. The results are shown in FIG. 3. As is obvious therefrom, the sample had 96.3% of its initial weight when 134 hours elapsed. The weight loss of the sample meant a reduction of 9.7% in weight of the perfume which is contained. In other words, as much as 90.3% by weight of the perfume still remained undiffused even after 134 hours.

EXAMPLE 6

A clathrate compound was prepared by repeating the process of EXAMPLE 4, except that a liquid perfume having the smell of lemon essence was employed. The infrared spectrum of the solidified product indicated that it was really a clathrate compound containing 43% by weight of lemon essence. It had the smell of lemon essence.

The procedure of EXAMPLE 4 was also repeated for determining the rate of diffusion. The results are shown in FIG. 3. As is obvious therefrom, the sample had 78.7% of its initial weight when 134 hours elapsed. The weight loss of the sample meant a reduction of 49.0% in weight of the perfume which it contained. In other words, 51.0% by weight of the perfume was still present even after 134 hours.

EXAMPLE 7

A clathrate compound was prepared by repeating the process of EXAMPLE 4, except that 1,8-cineole was now employed. The infrared spectrum of the solidified product confirmed that it was really a clathrate compound containing 54% by weight of cineole. It had the smell of cineole which was similar to that of camphor.

The procedure of EXAMPLE 4 was also repeated for determining the rate of diffusion. The results are shown in FIG. 3. As is obvious therefrom, the sample had 85.7% of its initial weight when 134 hours elapsed. The weight loss of the sample meant a reduction of 26.5% in weight of the perfume which it contained. In other words, 73.5% by weight of the perfume was still present even after 134 hours.

EXAMPLE 8

A 10 ml Erlenmeyer flask was charged with 0.206 g of 1,1,6,6-tetraphenyl-2,4-hexadiyne-1,6-diol and 0.41 ml of 1,8-cineole. The amount of the perfume was five times as large by molar ratio as that of the host compound. The flask was left at an ordinary room temperature (25° C.) and an atmospheric pressure for two weeks, whereby a precipitate was obtained. It had the smell of cineole which was similar to that of camphor. Its infrared spectrum confirmed that it was a clathrate compound.

EXAMPLE 9

A 10 ml Erlenmeyer flask was charged with 0.197 g of 1,1-di(2,4-dimethylphenyl)-1-propyne-1-ol and 0.65 ml of 1,8-cineole. The amount of the perfume was five times as large by molar ratio as that of the host compound. The flask was left to stand at an ordinary room temperature and an atmospheric pressure for two weeks, whereby a precipitate was obtained. It had the smell of cineole which was similar to that of camphor. Its infrared spectrum confirmed that it was a clathrate compound.

EXAMPLE 10

A 10 ml Erlenmeyer flask was charged with 0.198 g of N,N,N',N'-tetra(cyclohexyl)-(1,1'-biphenyl)-2,2'-dicarboxyamide and 0.30 ml of 1,8-cineole. The amount of the perfume was five times as large by molar ratio as that of the host compound. The flask was left to stand at an ordinary room temperature and an atmospheric pressure for two weeks, whereby a precipitate was obtained. It had the smell of cineole which was similar to that of camphor. Its infrared spectrum confirmed that it was a clathrate compound.

EXAMPLE 11

A mixture of 1.6 g of bis(4-hydroxyphenyl)sulfone and 1.0 g of cineole was stirred at an ordinary room temperature (25° C.), so that their reaction might take place. After about two hours, their reaction terminated with the precipitation of a white solid product. Its infrared spectrum confirmed that it was a clathrate compound containing 38% by weight of cineole, which compound will hereinafter be referred to as "cineole/(D)".

EXAMPLE 12

A mixture of 2.48 g of 4,4'-butylidenebis(6-tert-butyl-3-methylphenol) and 1.0 g of cineole was stirred at an ordinary room temperature. Their reaction proceeded rapidly and resulted in the precipitation of a white solid product. Its infrared spectrum confirmed that it was a clathrate compound containing 35% by weight of cineole, which will hereinafter be referred to as "cineole/(E)".

EXAMPLE 13

A mixture of 1.7 g of 2,2'-methylenebis(6-tert-butyl-4-methylphenol) and 1.04 g of cineole was stirred at an ordinary room temperature. Their reaction proceeded rapidly and resulted in the precipitation of a white solid product. Its infrared spectrum confirmed that it was a clathrate compound containing 38% by weight of cineole, which will hereinafter be referred to as "cineole/(F)".

EXAMPLE 14

A mixture of 1.8 g of 4,4'thiobis(6-tert-butyl-3-methylphenol) and 1.53 g of cineole was stirred at an ordinary room temperature. Their reaction was slow and resulted after one or two days in the precipitation of a white solid product. Its infrared spectrum confirmed that it was a clathrate compound containing 46% by weight of cineole, which will hereinafter be referred to as "cineole/(G)".

EXAMPLE 15

A sample of each of the clathrate compounds "cineole/(D)" to "cineole/(g)" which had been obtained in EXAMPLES 11 to 14, respectively, was placed in a laboratory dish and a reduction of its weight was measured at certain intervals of time in an open system having a temperature of 25° C. Each sample was compared with a sample consisting solely of cineole. The results are shown in FIG. 4.

Figure 4:
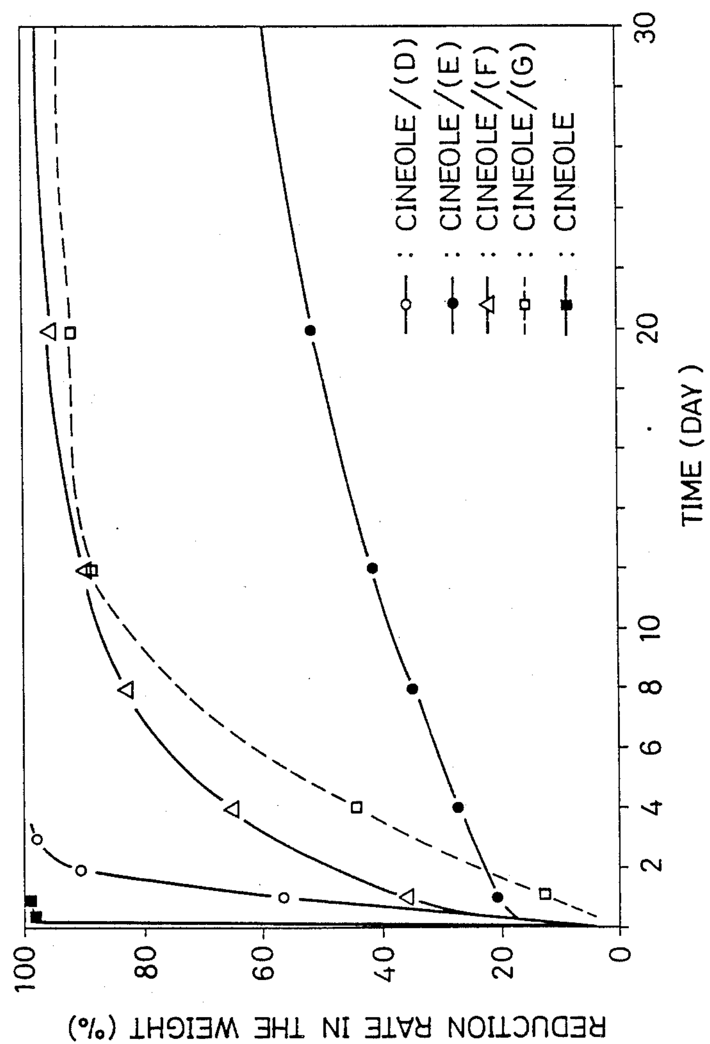
FIG. 4 is a graph showing the results which will be described as having been obtained in EXAMPLE 15.

As is obvious from FIG. 4, all of the clathrate compounds of EXAMPLES 11 to 14 allowed the imprisoned cineole to diffuse considerably slowly as compared with the diffusion of aroma from the sample consisting solely of cineole.

EXAMPLE 16

Figure 5:
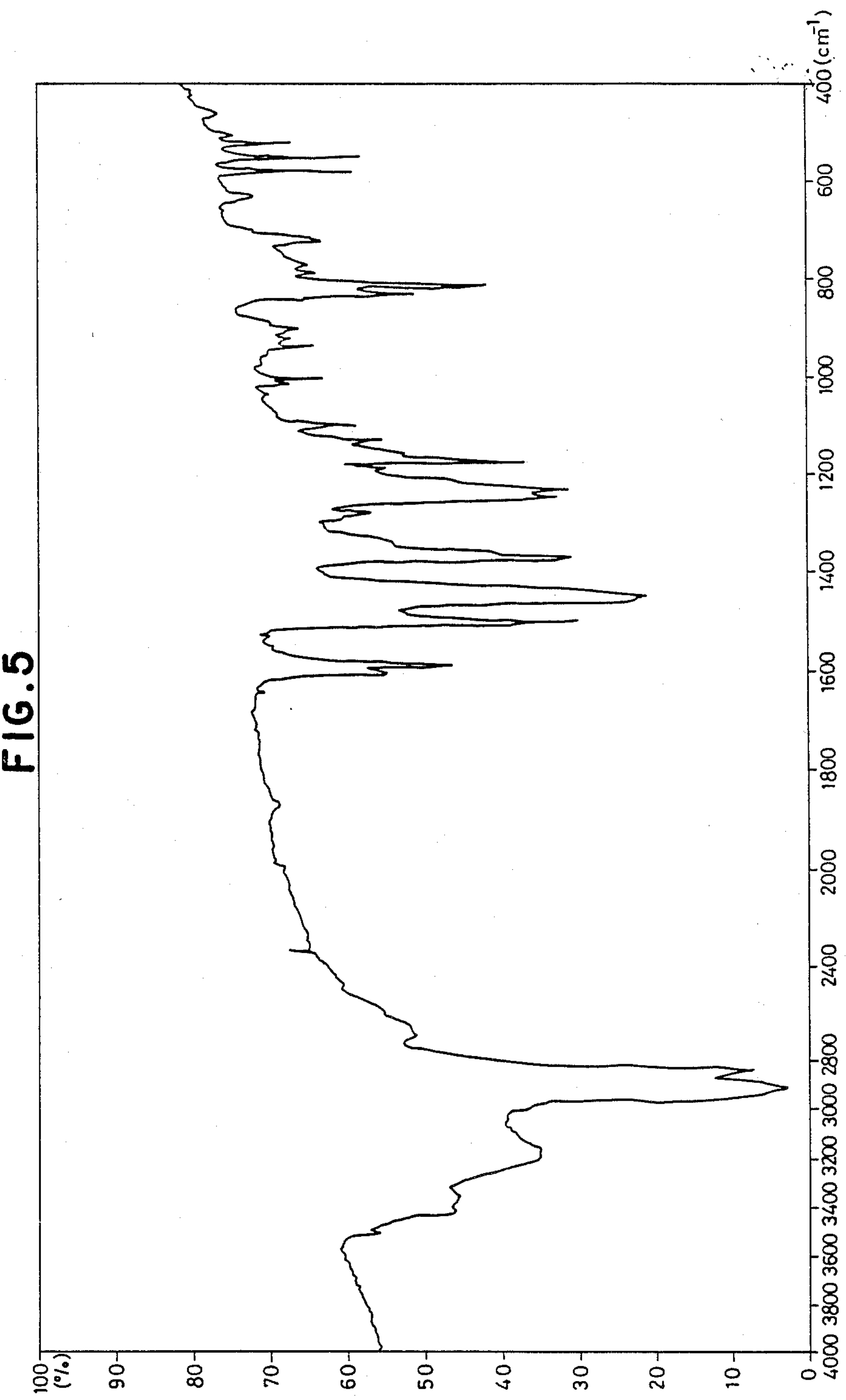
FIG. 5 is a chart showing the infrared spectrum of the clathrate compound which will be described as having been obtained in EXAMPLE 16.

0.48 g of α-terpineol was heated to a temperature of about 65° C. over a water bath, whereby it was melted. At the same temperature, 0.97 g of 4,4'-cyclohexylidene bisphenol was added to the molten terpineol and mixed carefully therewith. Their reaction proceeded rapidly and immediately resulted in the formation of a solid product. Its infrared spectrum (FIG. 5) confirmed that it was a clathrate compound containing 33.1% by weight of $\alpha$-terpineol.

Figure 6:
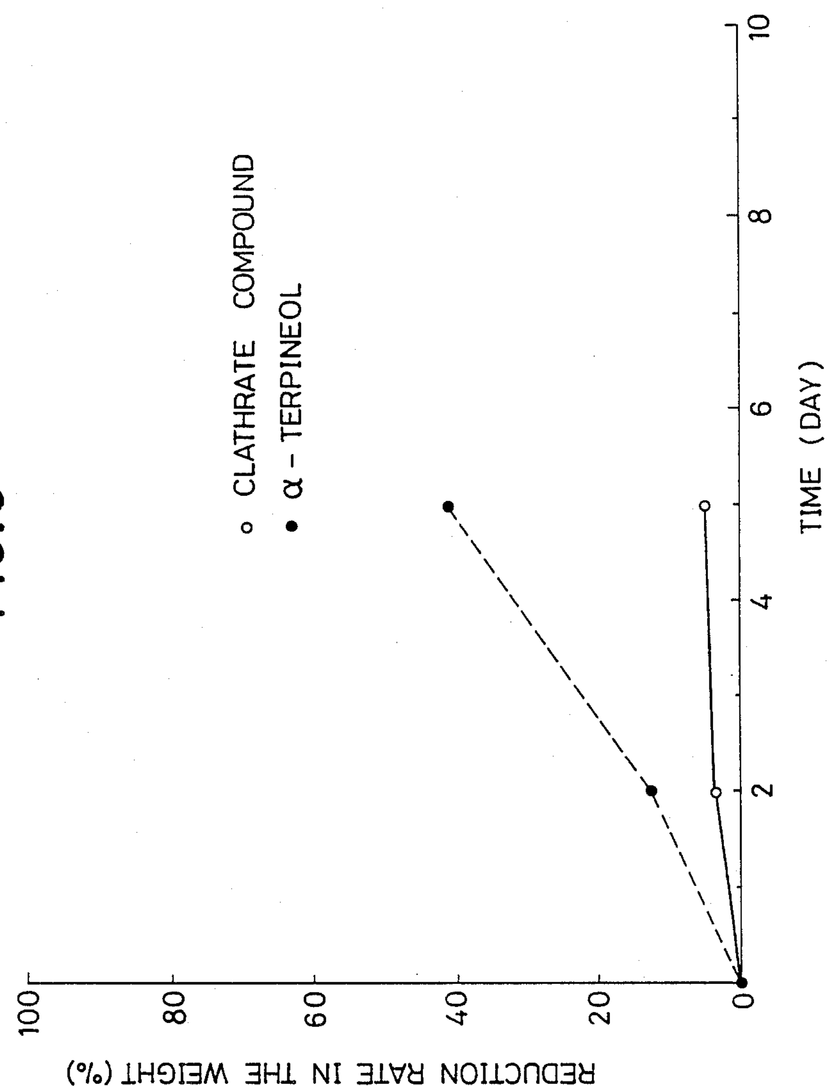
FIG. 6 is a graph showing the test results which will be described as having been obtained in EXAMPLE 16.

A sample of the clathrate compound weighing 1 g and a comparative sample of $\alpha$-terpineol weighing 0.3 g were each placed in a laboratory dish. Each sample was examined for the diffusion of aroma at an ordinary room temperature and an atmospheric pressure. For this purpose, a reduction in weight of each sample was measured at certain intervals of time. The results are shown in FIG. 6. Both of the samples continued giving out a smell peculiar to $\alpha$-terpineol throughout the duration of the tests. As is obvious from FIG. 6, however, the diffusion of $\alpha$-terpineol from the clathrate compound was slower than from the comparative sample.

EXAMPLE 17

Figure 7:
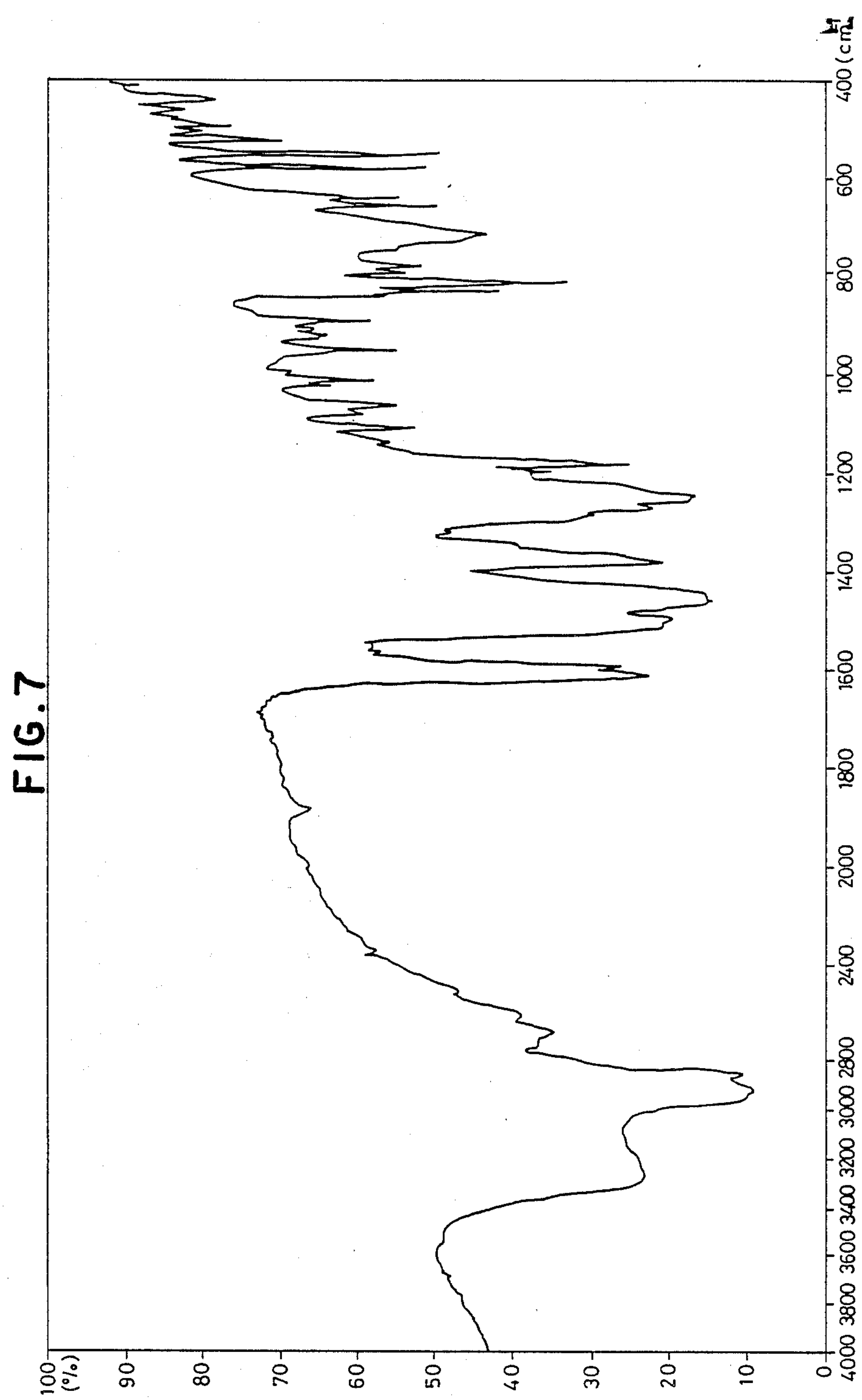
FIG. 7 is a chart showing the infrared spectrum of the clathrate compound which will be described as having obtained in EXAMPLE 17.

0.6 g of hinokitiol was melted by heating to a temperature of about 60° C. over a water bath. At the same temperature, 1.0 g of 4,4'-cyclohexylidene bisphenol was added to the molten hinokitiol and mixed carefully therewith. Their reaction was rapid and immediately formed a solid product. Its infrared spectrum (FIG. 7) confirmed that it was a clathrate compound containing 38.1% by weight of hinokitiol.

EXAMPLE 18

Four grams of l-menthol were melted by heating to a temperature of about 55° C. over a water bath. Five grams of 4,4'-cyclohexylidene bisphenol were added to the molten menthol and mixed carefully therewith. Their reaction was rapid and immediately formed a solid product. Its infrared spectrum confirmed that it was a clathrate compound containing 40.5% by weight of l-menthol.

What is claimed is:

1. A sustained release aromatic comprising a clathrate compound composed of a perfume and a polyphenyl compound, said polyphenyl compound being at least one compound selected from the group consisting of the compounds of formulas (I) to (VIII):

(I)

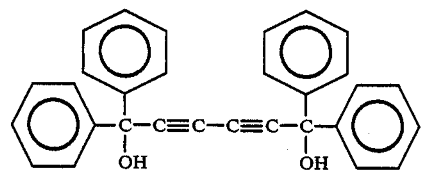

(II)

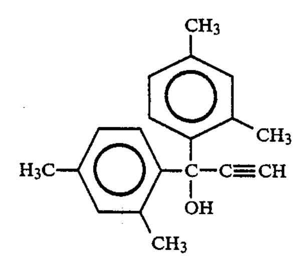

-continued (III)

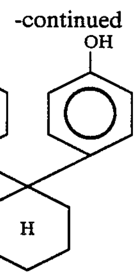

(IV)

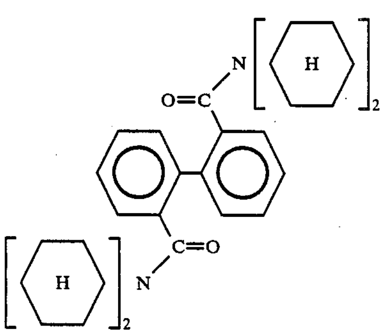

(V)

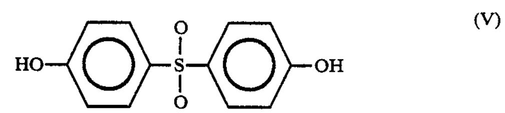

(VI)

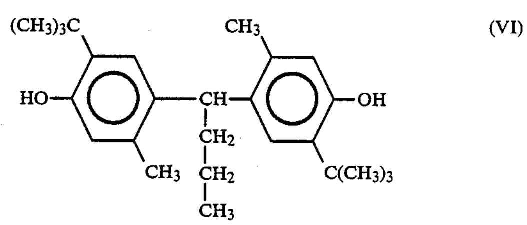

(VII)

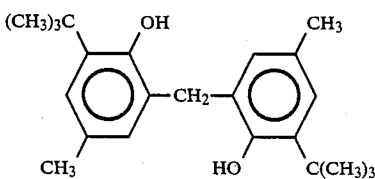

(VIII)

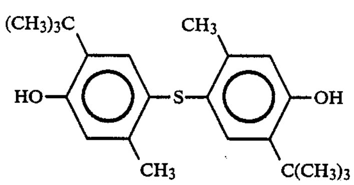

2. An aromatic as set forth in claim 1, wherein said perfume is at least one liquid perfume selected from the group consisting of cineole, hinoki oil, kinmokusei, jasmin, lemon, rose, rosemary, palmarosa oil, lavender, spearmint oil, mentha arbensis, l-$\alpha$-terpineol, l-methone, citronellal, d-pulegone, linalool oxide, cinnamon, quassia oil, menthol, Ceylon cinnamon, peppermint oil and l-carvone.

* * * * *